United States Patent [19]

Tchéraz

[11] Patent Number: 4,468,225
[45] Date of Patent: Aug. 28, 1984

[54] DEVICE FOR REGULATING THE LIQUID FLOW IN A PIPE

[75] Inventor: Patrick Tchéraz, Vandoeuvres, Switzerland

[73] Assignee: Etablissement Sideco International, Vaduz, Switzerland

[21] Appl. No.: 448,745

[22] Filed: Dec. 10, 1982

Related U.S. Application Data

[63] Continuation of Ser. No. 210,640, Nov. 26, 1980, abandoned.

[30] Foreign Application Priority Data

Nov. 27, 1979 [CH] Switzerland ............... 10541/79

[51] Int. Cl.³ ............................................. A61M 5/00
[52] U.S. Cl. .................................... 604/248; 251/149; 251/149.9; 251/208; 604/251; 604/905
[58] Field of Search ............... 604/32, 246, 248, 251, 604/252, 905; 251/149, 149.1, 149.5, 149.9, 208

[56] References Cited

U.S. PATENT DOCUMENTS

| 3,626,980 | 12/1971 | Svensson | 251/149 |
| 3,768,476 | 10/1973 | Raitto | 604/905 X |
| 3,877,428 | 4/1975 | Seagle et al. | 604/248 |
| 3,880,401 | 4/1975 | Wiltse | 604/248 X |
| 4,183,499 | 1/1980 | Swartz et al. | 251/208 |
| 4,366,816 | 1/1983 | Bayard et al. | 604/905 X |

FOREIGN PATENT DOCUMENTS 1114  3/1979  European Pat. Off. ........... 604/251

Primary Examiner—Dalton L. Truluck
Attorney, Agent, or Firm—Ladas & Parry

[57] ABSTRACT

It is intended to a probe, an apparatus for parenteral or enteral infusion.

Two bodies (1, 2) are nested one into the other. They comprise each an inner cylindrical flowing means (4, 11) engaged one into the other by one of the ends thereof (4b, 11b) until the respective closing plates thereof (8, 14) are in contact. The outer casings (3, 10) co-operate by the ends thereof (18, 20) so as to keep the two bodies (1, 2) in an engagement relationship. The two bodies (1, 2) rotatingly move one with respect to the other and hence allow to regulate the flow by variable juxtaposition of the half-moon openings (9, 15) arranged in the closing plates (8, 14).

3 Claims, 5 Drawing Figures

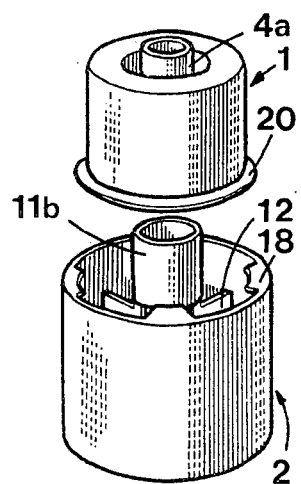
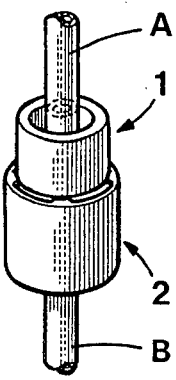
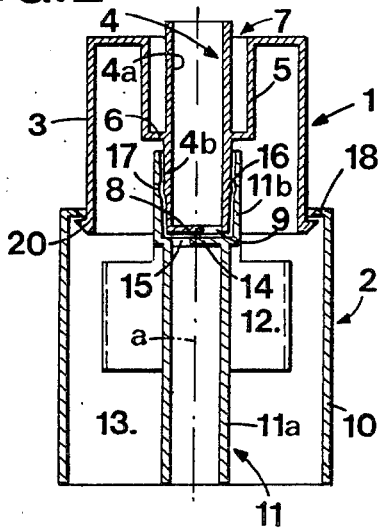
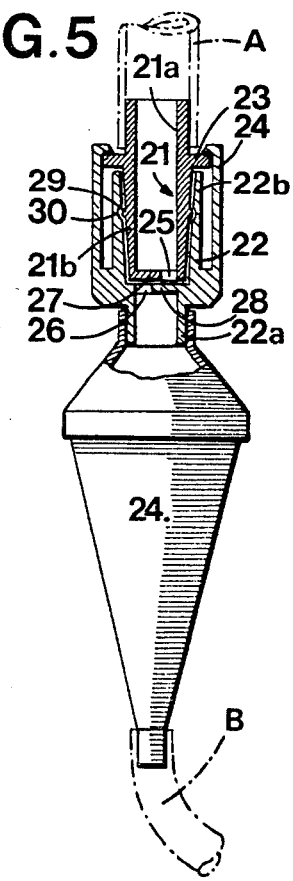
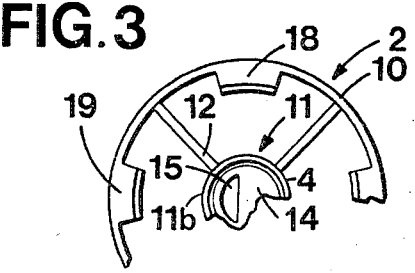

DEVICE FOR REGULATING THE LIQUID FLOW IN A PIPE

This is a continuation of application Ser. No. 210,640, filed Nov. 26, 1980, now abandoned.

The invention relates to a device for regulating the flow of a liquid in a pipe flowing under the influence of gravity, particularly in a flexible pipe of a probe, of an apparatus for parenteral and enteral infusion.

In the medical apparatus of this type, the flow is generally regulated by pinching the pipe by means of two parts which are tightened more or less by means of any screwing device. Such known devices are not very practical since the regulation of the flow varies according to the elasticity of the pipe.

There are also devices which are known (French Pat. No. 1.347.759), which comprise two cylindrical or conical bodies engaged one into the other so as to allow a relative movement therebetween, there being openings provided in the lateral wall of these bodies, which allow the regulation of the flow of liquid by bringing these openings into register more or less (or not at all for the closure). But it is very difficult to ensure a good sealing between the two bodies when they are made of cast plastic material; The liquid very often leaks when the device is in a closed position because the precision required to provide a good sealing cannot be obtained by casting such plastic material.

The present invention aims at solving this problem and at providing a simple device, inexpensive and practical, perfectly liquid-tight even when it is made by casting plastic material and comprised of two parts only, allowing the user there to stably regulate the liquid flow therethrough precisely and this, optionally, with one hand only.

Therefore, the object of the invention is to provide a device for regulating the liquid flow in a pipe as defined in claim 1.

In the annexed drawing showing two forms of execution of the object of the invention given as way of example:

FIG. 1 shows a perspective view of the two portions of a first form of execution of the object of the invention, FIG. 2 shows a cross-section view of the two parts engaged, FIG. 3 shows a top view of the lower part, FIG. 4 shows a perspective view of the two parts engaged, FIG. 5 shows a partial cross-section view of a second form of execution of the object of the invention, to which a droplet counter chamber has been attached.

FIGS. 1 to 4 show a first form of execution of the device according to the invention. It is comprised of an upper or upstream part 1 and of a lower or downstream part 2. Both parts are engaged one into the other and may pivot one with respect to the other. To that effect, each part carries an inner cylinder one of the extremities of which is fixed to a pipe and the other extremity of which is engaged in the corresponding extremity of the cylinder of the other part. Further, to allow this engagement, each part is composed of a cylindrical housing or casing integral with the inner cylinder. Thus, the upstream part formed of a single piece is comprised of a hollow body 1 and comprises a cylindrical outer casing 3 to which is secured the inner cylinder 4. Such securing is provided so as to delimit a part 4a to which a pipe may be fixed and a part 4b intended to be housed into the part 11b of the inner cylinder of the part 2 of the device. The cylindrical casing 3 may be folded on itself by the wall 5 and holds the inner cylinder 4 substantially at the middle thereof and further delimits, by an annular wall 6 an annular reception chamber 7 to receive the outer pipe A intended to be connected on the part 4a of the inner cylinder 4. The end of part 4b of the cylinder 4 is closed by a sealing plate 8 comprising a half-moon shaped opening 9. The downstream part, formed in a single piece consisting of the hollow body 2 comprises a cylindrical casing 10 and an inner cylinder 11. The latter is secured to the cylindrical casing 10 by three blades 12 arranged in a star configuration. These blades 12 are arranged substantially inwardly so as to leave a space 13 so that the end 11a of the cylinder 11 may receive a flow pipe B. The part 11b of the cylinder has a diameter slightly larger than the diameter of part 4b of cylinder 4 so as to receive and surround this cylindrical part 4b. The bottom of part 11b further comprises a sealing plate 14 and a half-moon shaped opening 15. Further, the part 4b has an annular bulging 16 intended to be accommodated in an annular groove 17. Once they are engaged, the groove 17 and the bulging 16 co-operate to ensure a better securing and a better sealing of the device. Further, the ends of each cylindrical casing 3 and 10 co-operate to provide this engagement. The cylindrical casing 10 comprises a series of ears or catches 18 arranged around the cylindrical casing 10 and extending inwardly. The extremity 11 of the catches 18 is arranged obliquely so as to better receive the end 20 of the other cylindrical casing 3. The latter comprises an annular edge 20 extending slightly outwardly. This edge 20 has a triangular section. Thus, owing to the symmetrical obliquity of the ends 18 and 20 of the cylindrical casings 3 and 10, it is easy to engage them by elastic deformation. After engagement, the sealing or closing plates 8 and 14 of parts 4b and 11b are touching each other and by rotation of the two bodies 1 and 2 with respect to each other, the half-moon shaped openings 9 and 15 may face each other.

The opening may be varied with the precision desired by the user.

FIG. 4 shows such an engaged or nested device connected to flow pipes A and B, these pipes A and B being simply inserted in parts 4a, and 11a of the device respectively.

In the embodiment of FIG. 5, the principle is the same. Two cylinders 21 and 22 are engaged or nested and are held one into the other by an annular edge or flange 23 formed integral with the cylinder 21 and by a skirt 24 integral with the cylinder 22 and closing slightly inwardly at the end thereof. The part 21a of the cylinder 21 is connected to a pipe A and the part 22a of the cylinder 22 is connected to a droplet counter chamber 24, itself being connected to the pipe B. The cylinder 22 may pivot with respect to the cylinder 21 and set the openings 25 and 26 of the bottom 27, respectively 28, facing each other. An annular bulge 29 and a groove 30 also co-operate to ensure the sealing between the parts 21 and 22 of the device.

In our example, a droplet counter chamber 24 has been arranged downstream of the cylinder 22 as an independent nested or engaged part. It is evident that such a chamber for counting the droplets may form, with the downstream part 22 or even with the upstream part 21, a single piece. The device for regulating the flow will still include in this case two nested parts but one of them being at the same time arranged as a droplet counter chamber.

In the forms of execution mentioned, the adjustment of the flow is effected by relative displacement of the two plates set inside of the conduit cylinders, said plates being provided with openings co-operating reciprocatingly.

The embodiment, by plastic material casting, of the devices disclosed with such plates (8, 14 respectively 27, 28) perfectly plane, raises no problem. Hence, the application of one of these plates against the other, ensures a good sealing and avoids any leak (caused by manufacturing inaccuracies) when the device is in a closed position.

The permanent application of one plate against the other, with a sufficient pressure, is ensured as soon as the parts 16, 17, resp. 29, 30 have been brought to the co-operation position thereof represented in the drawing.

It is clear that after engagement there must be a sufficient friction between the parts 1 and 2 so as to avoid any misregulation or misadjustment of the device during operation.

Such a device may be set along the perfusion apparatus or be directly incorporated in the droplet counter chamber and be an integral part of the latter.

It is also possible to incorporate in the device, either inside the cylinder 4 or the cylinder 11, a filter for the flowing solutions.

I claim:

1. Apparatus for regulating the flow of liquid from a first pipe to a second pipe, the liquid flowing under the influence of gravity, the apparatus consisting of a first and a second body each of one piece construction, rotatably engaged with one another and having a common axis, and wherein said first and second bodies comprise first and second central cylindrical flowing means respectively, connected to one of the pipes and having an axis coincident with the common axis of said first and second bodies; said first and second central cylindrical flowing means each comprising an end plate and at least one controlling passage; means for applying said end plates one against the other, the passage through said end plates having substantially the same cross-section for adjusting the flow through them from zero to a maximum when they are coincident, said cross-section being of the same magnitude as half the area of the plate; each of said first and second bodies further comprising an external cylindrical casing integral and coaxial with the respective flowing means and to be taken and actuated with one hand; and engaging means integral with said bodies being provided for maintaining said end plates in their abutting relationship.

2. An apparatus according to claim 1, wherein said first and second cylindrical flowing means engage one another in a sealing relationship.

3. An apparatus according to claim 1, wherein said first pipe and said second pipe are each secured to an extreme of said first and said second cylindrical flowing means, respectively.

* * * * *